(12) United States Patent
Capaldo et al.

(10) Patent No.: US 7,339,664 B2
(45) Date of Patent: Mar. 4, 2008

(54) SYSTEM AND METHOD FOR INSPECTING A LIGHT-MANAGEMENT FILM AND METHOD OF MAKING THE LIGHT-MANAGEMENT FILM

(75) Inventors: Kevin Patrick Capaldo, Mount Vernon, IN (US); Yu Hu, Evansville, IN (US); Chunghei Yeung, Evansville, IN (US); Yan Zhang, Shanghai (CN)

(73) Assignee: General Electric Company, Schenectady, NY (US)

( * ) Notice: Subject to any disclaimer, the term of this patent is extended or adjusted under 35 U.S.C. 154(b) by 387 days.

(21) Appl. No.: 10/952,651

(22) Filed: Sep. 29, 2004

(65) Prior Publication Data

US 2006/0066845 A1 Mar. 30, 2006

(51) Int. Cl.
*G01N 21/00* (2006.01)

(52) U.S. Cl. ............... 356/239.1; 356/239.2; 356/239.3; 356/239.8; 356/237.2; 382/141

(58) Field of Classification Search ......... 356/239.1, 356/239.2, 239.4, 239.8, 237.1, 237.2, 237.5, 356/430; 382/141
See application file for complete search history.

(56) References Cited

U.S. PATENT DOCUMENTS

| | | | | |
|---|---|---|---|---|
| 3,782,836 A | * | 1/1974 | Fey et al. ............... 356/237.2 |
| 4,310,242 A | | 1/1982 | Genco et al. ............ 356/128 |
| 4,595,289 A | * | 6/1986 | Feldman et al. ......... 356/237.5 |
| 5,146,282 A | | 9/1992 | Guering et al. .......... 356/239 |
| 5,175,030 A | | 12/1992 | Lu et al. .................. 428/30 |
| 5,183,597 A | | 2/1993 | Lu ........................... 264/1.4 |
| 5,271,968 A | | 12/1993 | Coyle et al. .............. 527/558 |
| 5,468,542 A | | 11/1995 | Crouch .................... 428/215 |
| 5,497,234 A | * | 3/1996 | Haga ....................... 356/239.3 |
| 5,626,800 A | | 5/1997 | Williams et al. .......... 264/1.38 |
| 5,691,811 A | | 11/1997 | Kihira ...................... 356/237 |
| 5,694,479 A | | 12/1997 | Guering et al. .......... 382/141 |
| 5,726,749 A | | 3/1998 | Schave ..................... 356/239 |
| 5,812,260 A | | 9/1998 | Louisnathan ............. 356/239 |
| 5,880,843 A | | 3/1999 | Hermosillo-Valadez et al. . 356/371 |
| 5,900,287 A | | 5/1999 | Williams | |
| 6,011,620 A | | 1/2000 | Sites et al. .............. 356/239.1 |

(Continued)

OTHER PUBLICATIONS

ASTM D 1003-00 pp. 1-6.

(Continued)

*Primary Examiner*—Gregory J. Toatley, Jr.
*Assistant Examiner*—Juan D Valentin, II
(74) *Attorney, Agent, or Firm*—Cantor Colburn LLP

(57) ABSTRACT

A method of inspecting a light-management film comprises reflecting light from an overhead light source off a first side of the light-management film and examining the light-management film for defects; directing transmission light from a backlight source through a second side of the light-management film to the first side and examining the light-management film for defects; reflecting light from the overhead light source off the second side of the light-management film and examining the light-management film for defects; directing transmission light from the backlight source through the first side of the light-management film to the second side and examining the light-management film for defects; and measuring a location of each of the examined defects in the light-management film.

9 Claims, 1 Drawing Sheet

U.S. PATENT DOCUMENTS

| | | | | |
|---|---|---|---|---|
| 6,208,412 | B1 | 3/2001 | Ladewski | 356/239.1 |
| 6,275,286 | B1 | 8/2001 | Haubold et al. | 356/239.1 |
| 6,280,063 | B1 | 8/2001 | Fong et al. | 362/333 |
| 6,563,577 | B2 * | 5/2003 | Oomori et al. | 356/237.2 |
| 6,577,756 | B1 * | 6/2003 | Furui | 382/141 |
| 6,618,136 | B1 * | 9/2003 | Ishida | 356/239.1 |
| 6,628,379 | B1 * | 9/2003 | Sudo et al. | 356/237.1 |
| 2003/0076489 | A1 * | 4/2003 | Tuttle et al. | 356/237.1 |
| 2003/0108710 | A1 | 6/2003 | Coyle et al. | 428/64.4 |
| 2004/0131245 | A1 | 7/2004 | Furui | |

OTHER PUBLICATIONS

JP2002148142 Publication Date.. May 22, 2002, Abstract Only.

JP2002365221 Publication Date Dec. 18, 2002 (Abstract Only).

Medical Device & Diagnostic Industry Magazine, MDDI Article Index, "Residual Stress Testing for Transparent Polymers", Alex S. Redner and Barbara Hoffman, http://www.devicelink.com/mddi/archive/99/03/008.html; Mar. 1999, 6 pages.

Archives, Nov. 2000, http://www.lasor.com/archives.html; 7 pages.

JP Publication No. 11 153515; Publication date Jun. 8, 1999; Apparatus and Method for Inspecting Color Filter; Inventor Yanai Hiroshi; Abstract; only 1 page.

JP Publication No. 09 033395; Publication Date Feb. 7, 1997; Inspection Shipping Device for View Finder Color Filter; Inventor: Hasegawa Jun; Abstract; only 1 page.

International Search Report; International Application No: PCT/US2005/033561; International Filing Date Sep. 19, 2005; Applicant's File Reference No. 08CS151145; Date of Mailing Jan. 10, 2006; 7 pages.

ASTM D 1003-00 pp. 1-6, Jun. 2004.

JP2002148142 Publication Date. May 22, 2002 Abstract Only.

* cited by examiner

SYSTEM AND METHOD FOR INSPECTING A LIGHT-MANAGEMENT FILM AND METHOD OF MAKING THE LIGHT-MANAGEMENT FILM

BACKGROUND

In flat panel displays (e.g., backlight computer displays), light-management film(s) (which can also be referred to as a sheets, layers, foils, and the like) are commonly used, for example, to direct, diffuse, and/or polarize light. For example, in backlight displays, a light-management film comprising a light-redirecting structure, which can also be referred to as a brightness enhancement film, can direct light along a viewing axis (i.e., an axis normal (perpendicular) to the display) using the light-redirecting structure (e.g., a prismatic structure). This enhances the brightness of the light viewed by the user of the display and allows the system to consume less power in creating a desired level of on-axis illumination. Such films can also be used in a wide range of other optical designs, such as in projection displays, traffic signals, and illuminated signs.

In making and/or handling the light-management film comprising the light-redirecting structure(s), various defects can be imparted to the light-management film. The light-redirecting nature of the light-management film can make inspection of these defects in the light-management film difficult. For example, the light-redirecting nature of the light-management film can cause unfocused images (e.g., blurred images, distorted images, and the like). Typical inspections by either human or cameras are not thorough enough to reliably capture all relevant defects in a given light-management film sample. This includes inspecting the film under a restricted (limited) set of viewing and lighting angles.

What is needed in the art is an improved system and method for inspecting a light-management film. More particularly, what is needed in the art is an improved system and method for inspecting a light-management film comprising a light-redirecting structure.

SUMMARY

Disclosed herein are system and methods for inspecting a light-management film, and method of making the light-management film.

One embodiment of a method of inspecting a light-management film comprises reflecting light from an overhead light source off a first side of the light-management film and examining the light-management film for defects; directing transmission light from a backlight source through a second side of the light-management film to the first side and examining the light-management film for defects; reflecting light from the overhead light source off the second side of the light-management film and examining the light-management film for defects; directing transmission light from the backlight source through the first side of the light-management film to the second side and examining the light-management film for defects; and measuring a location of each of the examined defects in the light-management film.

One embodiment of a system for inspecting a light-management film comprises a working plate comprising a first plate surface and a second plate surface; a backlight source disposed proximate to the second plate surface and in optical communication with the working plate, wherein the backlight source is capable of acting as a transmission light source such that transmission light can be transmitted through the second plate surface to the first plate surface; and an overhead light source disposed proximate to the first plate surface, wherein the overhead light source and the backlight source are disposed on opposite sides of the working plate, and wherein the overhead light source is capable of acting as a reflective light source such that reflective light can be reflected off the light-management film when the light-management film is disposed in physical communication with the first plate surface.

One embodiment of a method of making a light-management film comprises forming a light-management film comprising light-redirecting structures disposed on a surface of the light-management film; inspecting the light-management film, wherein inspecting comprises reflecting light from an overhead light source off a first side of the light-management film and examining the light-management film for defects; directing transmission light from a backlight source through a second side of the light-management film to the first side and examining the light-management film for defects; reflecting light from the overhead light source off the second side of the light-management film and examining the light-management film for defects; directing transmission light from the backlight source through the first side of the light-management film to the second side and examining the light-management film for defects; and measuring a location of each of the examined defects in the light-management film; classifying the examined defects; comparing the classified defects to a predetermined set of defects to determine the cause of the defects; and modifying a process condition in the forming of the light-management film based on the comparing of the classified defect to the predetermined set of defects.

The above-described and other features will be appreciated and understood by those skilled in the art from the following detailed description, drawings, and appended claims.

BRIEF DESCRIPTION OF THE DRAWINGS

Referring now to the figures, which are exemplary embodiments, and wherein the like elements are numbered alike.

DETAILED DESCRIPTION

Figure 1:
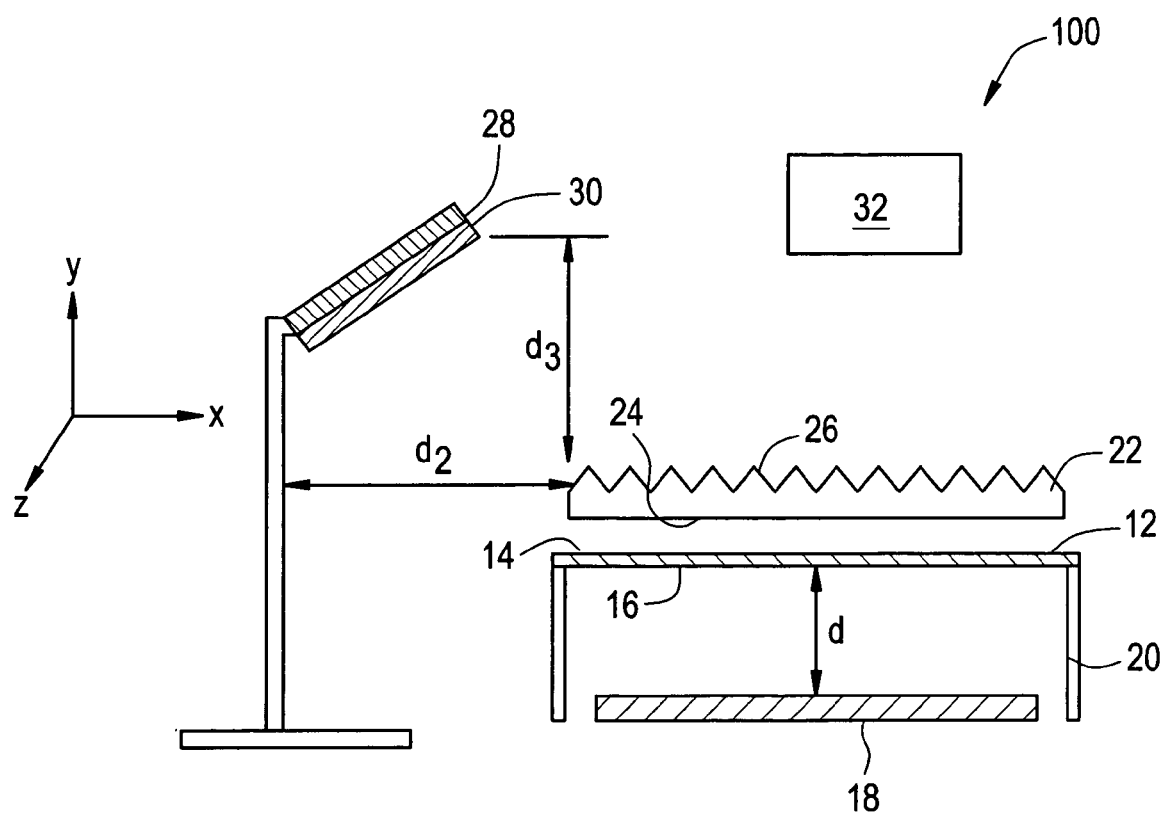
FIG. 1 is a schematic illustration of an embodiment of an inspection system for a light-management film.

It should first be noted that the terms "first," "second," and the like herein do not denote any order, quantity, or importance, but rather are used to distinguish one element from another, and the terms "a" and "an" herein do not denote a limitation of quantity, but rather denote the presence of at least one of the referenced item. Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," is inclusive of the endpoints and all intermediate values of the ranges, e.g., "about 5 wt. % to about 25 wt. %, about 5 wt. % to about 15 wt. %," etc.).

Disclosed herein is a system and method for inspecting a light-management film and method of making the light-management film. It is to be understood that references made to a light-management film in relation to a backlight display are merely for convenience in discussion, and that other applications are envisioned to be within the scope of this disclosure. Moreover, while the light-management film is discussed in relation to a light-management film comprising a light-redirecting structure, it is to be understood that the system and method can be adapted for use with other light-management films (e.g., a multi-functional brightness enhancement films comprising a prismatic first surface and a textured second surface, and the like).

In an embodiment, the light-management film can comprise a light-redirecting structure (e.g., a prismatic (pyramid-like) structure, cube corners, spheres, edges, and the like) to direct light along the viewing axis (i.e., normal to the display). Generally, the light-management film comprises a base film that can comprise an optional curable coating disposed thereon. The light-redirecting structure can be created, for example, by applying the curable coating to the base film and casting the desired light-redirecting structure in the curable coating, by hot-embossing the structure directly onto the base film, or the like. While the base film material can vary depending on the application, suitable materials include those transparent base film materials discussed in published U.S. patent application No. 2003/0108710 to Coyle et al. More specifically, the base film material of the light-management film can comprise, acrylics, polycarbonates, phenolics, cellulose acetate butyrate, cellulose acetate propionate, poly(ether sulfone), poly(methyl methacrylate), polyurethane, polyester, poly(vinylchloride), polyethylene terephthalate, and the like, as well as blends, copolymers, reaction productions, and combinations comprising at least one of the foregoing.

The optional curable coating can comprise a curable composition, which generally comprises a polymerizable compound. Polymerizable compounds, as used herein, include monomers or oligomers comprising one or more functional groups capable of undergoing radical, cationic, anionic, thermal, and/or photochemical polymerization. Suitable functional groups include, for example, acrylate, methacrylate, vinyl, epoxide, and the like.

For example, the curable composition can include monomeric and dimeric acrylates, for example, cyclopentyl methacrylate, cyclohexyl methacrylate, methylcyclohexylmethacrylate, trimethylcyclohexyl methacrylate, norbornylmethacrylate, norbornylmethyl methacrylate, isobornyl methacrylate, lauryl methacrylate 2-ethylhexyl methacrylate, 2-hydroxyethyl methacrylate, hydroxypropyl acrylate, hexanediol acrylate, 2-phenoxyethyl acrylate, 2-hydroxyethyl acrylate, 2-hydoxypropyl acrylate, diethyleneglycol acrylate, hexanediol methacrylate, 2-phenoxyethyl methacrylate, 2-hydroxyethyl methacrylate, 2-hydoxypropyl methacrylate, diethyleneglycol methacrylate, ethylene glycol dimethacrylate, ethylene glycol diacrylate, propylene glycol dimethacrylate, propylene glycol diacrylate, allyl methacrylate, allyl acrylate, butanediol diacrylate, butanediol dimethacrylate, 1,6hexanediol diacrylate, 1,6-hexanediol dimethacrylate, diethyleneglycol diacrylate, trimethylpropane triacrylate, pentaeryritol tetraacrylate, hexanediol dimethacrylate, diethyleneglycol dimethacrylate, trimethylolpropane triacrylate, trimethylpropane trimethacrylate, pentaeryritol tetramethacrylate, and combinations comprising at least one of the foregoing acrylates.

Methods of coating a curable composition on a surface of a base film (substrate) are described, for example, in U.S. Pat. No. 5,175,030 to Lu et al., U.S. Pat. No. 5,183,597 to Lu, U.S. Pat. No. 5,271,968 to Coyle et al., U.S. Pat. No. 5,468,542 to Crouch, U.S. Pat. No. 5,626,800 to Williams et al., and U.S. Pat. No. 6,280,063 to Fong et al., as well as U.S. patent aplication Publication No. 2003/0108710 A1 to Coyle et al. For example, suitable methods of disposing the coating on the base film include, but are not limited to, spraying, brushing, electro-deposition, dipping, flow coating, roll coating, gravure, and screen printing.

In other embodiments, the light-redirecting structures can be formed by hot-embossing the base film. For example, the method can comprise heating the base film to a temperature sufficient to soften the base film, and embossing the desired structure into the base film. It is noted that roll embossing, stamping, or the like can be employed to emboss the light-redirecting structure (e.g., prism(s)) into the base film. More particularly, the embossing tool comprises a negative image of the desired surface.

Regardless of the method of making the light-management film, various defects can be imparted to the light-management film as part of the manufacturing process and/or handling process. As will be described in greater detail below, a system and method of inspecting a light-management film has been discovered that allows defects to be detected in a light-management film using both transmission light and reflective light over a wide range of viewing angles.

Referring now to FIG. 1, an exemplary system for inspecting a light-management film, generally designated 100, is illustrated. The system 100 comprises a working plate (film) 12 comprising a first plate surface 14 and a second plate surface 16, wherein the working plate 12 is disposed in optical communication and/or physical communication with a backlight source 18. For example, the backlight source 18 can be disposed a sufficient distance, "d", from the second plate surface 16 of the working plate 12 to allow light to be transmitted through the second plate surface 16 and through the first plate surface 14. Optionally, the working plate 12 can be disposed in physical communication with a support 20 (e.g., a rack, and the like) such that the distance "d" can be created between the second plate surface 16 and the backlight source 18. In yet another embodiment, the backlight source can be a liquid crystal display (LCD) backlight assembly, such as those used in computer displays, with the light management films removed and replaced with the work piece (e.g., light-management film 22).

During inspection, the work piece, e.g., a light-management film 22 comprising a first light-management film surface 24 and a second light-management film surface 26 comprising light-redirecting structure(s) (hereinafter referred to as a light-redirecting surface 26), can be disposed in optical and/or physical communication with the first plate surface 14 of the working plate 12. Generally, the working plate 12 comprises a size and shape greater than or equal to the overall size and shape of the light-management film 22. For example, the working plate 12 can comprise a rectangular shape, and the like.

Furthermore, disposed in optical communication with the light-management film 22 is an overhead light source 28. Optionally, a light-diffusing film 30 can be disposed in physical and/or optical communication with light source 28 to aid in distributing the light from the overhead light source 28 to the light-management film 22. The overhead light source 28 can be positioned relative to the light-management film 22 and the working plate 12 such that the overhead light source 28 can provide a source of reflective light for the inspection of the light-management film 22. More particularly, the overhead light source 28 can be disposed proximate a side of the working plate 12 (e.g., first plate surface 14) opposite a side of the working plate 12 proximate to the backlight source 18 (e.g., second plate surface 14).

Furthermore, the overhead light source 28 can be positioned at an angular off-set from the working plate 12 and the light-management film 22 such that overhead light source 28 can act as a reflective light source. In other words, the overhead light source 28 can be disposed a distance, "$d_2$", from an edge of the light-management film 22 and/or and edge of working plate 12 in a horizontal direction ("x" direction); and can be disposed a distance, "$d_3$" from an edge of the light-management film 22 and/or edge of working plate 12 in a vertical direction. It is noted that the distances "$d_2$" and "$d_3$" are provided in FIG. 1 merely for ease in discussion. It is to be understood that any reference point relative to the light source 28 and the light-management film can be employed to position the light source 28 such that the light source 28 is capable of acting as a reflective light source.

For example, in an embodiment, the overhead light source 28 is positioned relative to the light-management film 22 such that the overhead light source 28 is disposed a distance, "$d_2$", up to about 2.0 feet (ft) (about 0.61 meters (m)) from an edge of the light-management film 22 in a horizontal direction (e.g., in the "x" direction) and a distance, "$d_3$", up to about 2.0 ft (about 0.61 m) from the edge of the light-management film 22 in a vertical direction (e.g., in the "y" direction). More particularly, the overhead light source 28 is disposed a distance of about 1.5 ft (about 0.46 m) to about 2.0 ft (about 0.61 m) from the edge of the light-management film 22 in the horizontal direction and a distance of about 1.5 ft (about 0.46 m) to about 2.0 ft (about 0.61 m) from the edge of the light-management film 22 in the vertical direction.

A viewer 32 is positioned relative to the light-management film 22 such that defects in the light-management film 22 can be detected (observed) at a viewing angle of about 0° to about 90° in both the horizontal direction ("x" direction) and the depth direction (e.g., the "z" direction). While the viewer 32 can be a device (e.g., an optical camera, and the like) in some embodiments, the viewer 32 is desirably a human. It is noted that a human can advantageously view defects more quickly than, for example, an optical camera. More particularly, some defects may only be detectable (observable) at a particular viewing angle. It is easier for human to change view angles than the camera system.

In various embodiments, the working plate 12 can desirably comprise light-diffusing properties to aid in distributing light to the light-management film 22. In other words, the working plate 12 can act as a light-diffusing film. It is briefly noted that various techniques can be utilized to obtain films with light-diffusing capabilities. For example, physical modifications to the films can result in imprinting a texture to the surface of the film to diffuse light (e.g., textured light-diffusing films). In other embodiments, light-diffusing particles can be imbedded into the film to give the film light-diffusing properties (e.g., bulk light-diffusing films). In yet other embodiments, a combination of both methods can be used, i.e., both imprinting a texture on the surface of the film and imbedding a light-diffusing particle in the film.

In an exemplary embodiment, the working plate 12 can be selected to model the light-diffusing properties of a "bottom" light-diffusing film employed in a backlight display device. More particularly, the working plate 12 can comprise a haze value of greater than or equal to 90%, more particularly a haze value of greater than or equal to 95%.

It is noted that the percent haze can be predicted and calculated from the following equation:

$$\% \text{ Haze} = 100 \times \frac{\text{Total Diffuse Transmission}}{\text{Total Transmission}} \quad (1)$$

wherein total transmission is the integrated transmission; and the total diffuse transmission is the light transmission that is scattered by the film as defined by ASTM D 1003.

Further, the working plate 12 can desirably be a scaled working plate. More particularly, the working plate 12 can comprise a scale disposed, for example, about a periphery of the working plate 12. The scale can be employed to measure the location of a defect in the light-management film 22. Additionally and/or alternatively, the scale can be independent of the working plate 12. For example, the scale can be a transparent ruler, and the like. In various embodiments, support pads can be disposed at the ends of the ruler such that the ruler can be elevated over the light-management film 22 to prevent scratching of the light-management film 22. As will be described in greater detail below, by accurately measuring the location of a given defect in a light-management film, repeating defects in multiple films can be identified.

Backlight source 18 and overhead light source 28 can include both high-brightness and low brightness light sources. The high-brightness light source can include, but is not limited to, a cold cathode fluorescent lamp, a fluorescent lamp, and the like. The low-brightness light source can include, but is not limited to, a light emitting diode (LED). It is noted that the backlight source 18 can be a source of transmission light (e.g., light passing through the light-management film), whereas overhead light source 28 can be a source of reflective light (e.g., light reflected from a surface of the light-management film).

In an embodiment of a method of inspecting the light-management film comprising the light-redirecting structure (s), the method comprises 1) inspecting the light-management film at a viewing angle of about 0° to about 90° in the "x" direction and/or the "z" direction using reflective light when the light-redirecting structures are facing upward (i.e., in a direction facing away from a viewer); 2) inspecting the light-management film at a viewing angle of about 0° to about 90° in the "x" direction and/or the "z" direction using transmission light when the light-redirecting structures are facing upward; 3) inspecting the light-management film at a viewing angle of about 0° to about 90° in the "x" direction and/or the "z" direction using reflective light when the light-redirecting structure are facing downward (i.e., in a direction facing toward the viewer); and 4) inspecting the light-management film at a viewing angle of about 0° to about 90° in the "x" direction and/or the "z" direction using transmission light when the light-redirecting structures are facing downward.

In describing exemplary embodiments of the method below, reference is made to the above referenced method steps merely for convenience in discussion, it is noted that the order of these steps can vary depending on, for example, the given human inspector inspecting the light-management film, and the like. Furthermore, while it is noted that embodiments are envisioned wherein the light-management film is viewed in the "x" direction or the "z" direction, it is to be understood by those skilled in the art that by viewing the light-management film in both "x" direction and the "z" direction more defects can be identified compared to viewing the light-management film only in a single direction.

In an embodiment, during steps 1-2 of the inspection method, the first light-management film surface 24 is oriented such that the first light-management film surface 24 faces away from the viewer 32. More particularly, the first light-management film surface 24 can be disposed in physical communication with the first plate surface 14. In steps 3-4, the first light-management film surface 24 is oriented such that the first light-management film surface 24 faces toward the viewer 32. In other words, the light-redirecting surface 26 faces away from the viewer 32. More particularly, the light-redirecting surface 26 can be disposed in physical communication with the first plate surface 14. In step 1 and step 3, the backlight source 18 is "off" (i.e., backlight source 18 is not transmitting light) and overhead light source 28 is "on" (i.e., overhead light source 28 is transmitting light). Conversely, in steps 2 and 4, the backlight is "on" ant the overhead light is "off".

Without being bound by theory, when the backlight source 18 is "off" and the overhead light source 28 is "on", the position of the overhead light source 28 relative to the light-management film 22 allows the overhead light source 28 to act as a reflective light source. Further, when the backlight source 18 is "on" and the overhead light source 28 is "off", the backlight source 18 can act as a transmission light source. As such, this method allows the viewer 32 to detect both defects observable by reflective light and defects observable by transmission light. Since some defects may be observable using one light source and not the other, additional defects can be detected compared to systems and methods employing only one light source (e.g., only a backlight source).

Furthermore, as briefly noted above, this system and method allows the viewer 32 to detect defects in the light-management film 22 in both the "x" direction and the "z" direction over viewing angles of about 0° to about 90° in each respective direction. Again, some defects may only be detectable (observable) at a particular viewing angle. This system and method allows the viewer 32 to detect defects over a wide range of viewing angles in both the "x" direction and the "z" direction. As such, more defects can be detected compared to systems and methods wherein the viewer 32 can only detect defects at a particular viewing angle (e.g., a viewing angle normal to the light-management film).

In steps 1-4, the location of a defect within the light-management film can readily be determined by employing the scale and/or ruler as described above. Having determined the location of a defect in the light-management film, the method of inspecting the light-management film can further comprise classifying the defect according to type and severity. More particularly, with regards to defect type, a defect can be characterized as a handling defect, a processing defect, and the like. Furthermore, it is noted that processing defects can further be characterized as a repeating defect and a non-repeating defect.

Without being bound by theory, repeating defects can occur when a rotating processing roll used in making the light-management film has a contaminant thereon (e.g., a piece of dirt, and the like) and the contaminant contacts a surface of the light-management film. Additionally, repeating defects can also occur as a result of hardware defects, e.g., a worn roll, and the like. It is noted that repeating defects can be reproduced at predetermined distance intervals on the light-management film. For example, repeating defects can include scratches, dimples, imprints, straight lines, white specks, smudges, and the like.

In contrast to repeating defects, non-repeating defects are any point defects on the light-management film that are not caused by the processing rolls. Non-repeating defects are generally caused by contamination of particles within or on the light-management film and are not reproduced at pre-determined distance intervals on the light-management film. For example, non-repeating defects include a black spot, a white spot, a scratch, orange peel, air bubbles, flakes, black/brown region on the film surface or in the film, and the like.

Having determined the location of the defect(s) in the light-management film, the inspection method can further comprise comparing the location of the defect(s) in a first film to the location of the defect(s) in at least a second film. By comparing the location of defects in multiple films, repeating defects can be identified. More particularly, mathematical analysis (e.g., statistical analysis) can be employed to determine for example, the frequency of a given defect over a number of films, the probability of a film having a particular defect, and the like. It has further been discovered that analysis of the location of the defect in the light-management film can be used to identify the root cause of defects in the light-management film. More particularly, defect location in the light-management film can be correlated to various processing conditions as described above (e.g., repeating defects caused by a contaminant on a processing roll). The defects can be grouped according to the type and severity of the defect, and mathematical analysis can be employed to correlate a given type and severity of the defect to a given processing condition. Having identified the root cause of a given group of defects, the processing condition can be modified to mitigate/eliminate the given group of defects. As such, a higher yield of light-management films can be obtained when compared to traditional systems that do not use an inspection method to modify the processing conditions.

In an embodiment, intentionally designed experiments are run to determine the root cause of a given type and severity defect. Having correlated the given type and severity defect to a processing condition(s) (i.e., having determined the root cause of the group of defects) with these experiments, the processing condition employed in making the light-management film can be modified. More particularly, a classification system of defects is established, wherein each group of defects is associated with a given processing condition and/or set of processing condition. As such, a method of making a light-management film can comprise inspecting a light-management film employing the above system and/or method, comparing a defect to a pre-determine type and severity defect that is associated with a processing condition, and modifying the processing condition.

EXAMPLES

In this example, 13 different types of defects have been identified. Table 1 showed the definitions of these defects.

TABLE 1

| Defect Type | Brief Description |
|---|---|
| Point Defects | Black, brown, amber, white, and the like spot(s), which can be caused by pressing, abrading, imprinting, and the like. |
| Bend | Light line, which can be caused by handling, masking removing, and the like. |
| Scratch | Irregular lines caused by tools and handling. |
| Smudge/Bruise/Dirt | Shown as white/gray fuzzy area. |
| Dimple | Dimples are those shadowed indent in the films, generally with round edge. |

TABLE 1-continued

| Defect Type | Brief Description |
| --- | --- |
| Form | Short line defect along the optical line of the prism. |
| Orange Peel | A bunch of continuous dimples. The film looks like orange skin against reflective light. |
| White Straight Line | The line across the whole web |
| Murm | An obvious gray line. |
| Shadow Band | A broad shadow area across the patch. |
| Imprint | Shadow indent with irregular shapes. |
| Ripple | Elongated deformation or waving |
| Others | Anything not listed above |

In contrast to the inspection method disclosed herein, traditional inspection methods generally detected only 4 of the above identified defects (Point Defects, Bend, Scratch, and Smudge/Bruise/Dirt). For example, a traditional method of inspecting a light-management film comprised installing the light-management film in an LCD backlight display and inspecting the film using transmitted light only.

Advantageously, the system and method of inspecting a light-management film disclosed herein allows a viewer (e.g., human inspector) to detect defects in the light-management film using both reflective light and transmission light. Since some defects may be observable using one light source and not the other, additional defects can be detected compared to systems and methods employing only one light source (e.g., only a backlight source). Furthermore, this system and method allows the viewer to detect defects over a wide range of viewing angles in both the "x" direction and the "z" direction. As such, more defects can be detected compared to systems and methods wherein the viewer can only detect defects at a particular viewing angle (e.g., a viewing angle normal to the light-management film). Moreover, the inspection method can be used to track the root cause of the defect and thereby modify processing conditions to avoid further defects.

While the invention has been described with reference to several embodiments thereof, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A system for inspecting a light-management film, the system comprising:
    a working plate comprising a first plate surface and a second plate surface wherein the working plate comprises light diffusing properties;
    a backlight source disposed proximate to the second plate surface and in optical communication with the working plate, wherein the backlight source is capable of acting as a transmission light source such that transmission light can be transmitted through the second plate surface to the first plate surface; and
    an overhead light source disposed proximate to the first plate surface, wherein the overhead light source and the backlight source are disposed on opposite sides of the working plate, and wherein the overhead light source is capable of acting as a reflective light source such that reflective light can be reflected off the light-management film when the light-management film is disposed in physical communication with the first plate surface.

2. A system for inspecting a light-management film, the system comprising:
    a working plate comprising a first plate surface and a second plate surface, wherein the working plate comprises a scale;
    a backlight source disposed proximate to the second plate surface and in optical communication with the working plate, wherein the backlight source is capable of acting as a transmission light source such that transmission light can be transmitted through the second plate surface to the first plate surface; and
    an overhead light source disposed proximate to the first plate surface, wherein the overhead light source and the backlight source are disposed on opposite sides of the working plate, and wherein the overhead light source is capable of acting as a reflective light source such that reflective light can be reflected off the light-management film when the light-management film is disposed in physical communication with the first plate surface.

3. A system for inspecting a light-management film, the system comprising:
    a working plate comprising a first plate surface and a second plate surface;
    a backlight source disposed proximate to the second plate surface and in optical communication with the working plate, wherein the backlight source is capable of acting as a transmission light source such that transmission light can be transmitted through the second plate surface to the first plate surface;
    an overhead light source disposed proximate to the first plate surface, wherein the overhead light source and the backlight source are disposed on opposite sides of the working plate, and wherein the overhead light source is capable of acting as a reflective light source such that reflective light can be reflected off the light-management film when the light-management film is disposed in physical communication with the first plate surface; and
    an overhead light diffusing film disposed in optical communication with the overhead light source.

4. The system of claim 1, further comprising a working plate support disposed in physical communication with working plate.

5. A method of inspecting a light-management film, the method comprising:
    reflecting light from an overhead light source off a first side of the light-management film and examining the light-management film for defects;
    directing transmission light from a backlight source through a work plate then through the second side of the light-management film to the first side and examining the light-management film for defects;
    reflecting light from the overhead light source off the second side of the light-management film and examining the light-management film for defects;
    directing transmission light from the backlight source through the first side of the light-management film to the second side and examining the light-management film for defects; and
    measuring a location of each of the examined defects in the light-management film;
    wherein the work plate comprises light diffusing properties.

6. A method of inspecting a light-management film, the method comprising:
- reflecting light from an overhead light source off a first side of the light-management film and examining the light-management film for defects;
- directing transmission light from a backlight source through a work plate then through a second side of the light-management film to the first side and examining the light-management film for defects, wherein the work plate comprises light a scale;
- reflecting light from the overhead light source off the second side of the light-management management film and examining the light-management film for defects;
- directing transmission light from the backlight source through the first side of the light-management film to the second side and examining the light-management film for defects; and
- measuring a location of each of the examined defects in the light-management film.

7. A method of inspecting a light-management film, the method comprising:
- reflecting light from an overhead light source off a first side of the light-management film and examining the light-management film for defects;
- directing transmission light from a backlight source through a work plate then through a second side of the light-management film to the first side and examining the light-management film for defects;
- reflecting light from the overhead light source off the second side of the light-management film and examining the light-management film for defects;
- directing transmission light from the backlight source through a work plate then through the first side of the light-management film to the second side and examining the light-management film for defects; and
- determining a location of each of the examined defects in the light-management film;
- wherein the work plate further comprises light diffusing properties.

8. A method of inspecting a light-management film, the method comprising:
- reflecting light from an overhead light source off a first side of the light-management film and examining the light-management film for defects;
- directing transmission light from a backlight source through a work plate then through a second side of the light-management film to the first side and examining the light-management film for defects;
- reflecting light from the overhead light source off the second side of the light-management film and examining the light-management film for defects;
- directing transmission light from the backlight source through a work plate then through the first side of the light-management film to the second side and examining the light-management film for defects; and
- determining a location of each of the examined defects in the light-management film;
- wherein the work plate further comprises a scale and light diffusing properties.

9. A method of inspecting a light-management film, the method comprising:
- reflecting light from an overhead light source off a first side of the light-management film and examining the light-management film for defects;
- directing transmission light from a backlight source through a work plate then through a second side of the light-management film to the first side and examining the light-management film for defects;
- reflecting light from the overhead light source off the second side of the light-management film and examining the light-management film for defects;
- directing transmission light from the backlight source through a work plate then through the first side of the light-management film to the second side and examining the light-management film for defects; and
- determining a location of each of the examined defects in the light-management;
- wherein the work plate further comprises a scale.

* * * * *